(12) United States Patent
Chu et al.

(10) Patent No.: US 9,341,745 B2
(45) Date of Patent: May 17, 2016

(54) 3D NETWORK-STRUCTURED SILICON-CONTAINING PREPOLYMER AND METHOD FOR FABRICATING THE SAME

(71) Applicant: UNICON OPTICAL CO., LTD., Hsinchu County (TW)

(72) Inventors: Shih-Hong Chu, Hsinchu County (TW); Hung-Hsuan Cheng, Changhua County (TW)

(73) Assignee: Unicon Optical Co., Ltd., Hsinchu County (TW)

( * ) Notice: Subject to any disclaimer, the term of this patent is extended or adjusted under 35 U.S.C. 154(b) by 0 days.

(21) Appl. No.: 14/791,637

(22) Filed: Jul. 6, 2015

(65) Prior Publication Data
US 2015/0309212 A1    Oct. 29, 2015

Related U.S. Application Data

(63) Continuation-in-part of application No. 14/202,144, filed on Mar. 10, 2014, now abandoned.

(51) Int. Cl.
| | | |
|---|---|---|
| C09D 183/00 | (2006.01) |
| G02B 1/04 | (2006.01) |
| C07F 7/18 | (2006.01) |
| C07F 7/08 | (2006.01) |
| C08L 83/08 | (2006.01) |
| C08G 77/26 | (2006.01) |

(52) U.S. Cl.
CPC ............. *G02B 1/043* (2013.01); *C07F 7/0821* (2013.01); *C07F 7/184* (2013.01); *C07F 7/1892* (2013.01); *C08L 83/08* (2013.01); *C08G 77/26* (2013.01)

(58) Field of Classification Search
CPC .... C08G 77/20; C08F 230/08; C08F 290/068
See application file for complete search history.

(56) References Cited

FOREIGN PATENT DOCUMENTS

CN          101279212       * 10/2008

* cited by examiner

*Primary Examiner* — Kuo-Liang Peng
(74) *Attorney, Agent, or Firm* — Rosenberg, Klein & Lee

(57) ABSTRACT

A 3D network-structured silicon-containing preploymer and a method for fabricating the same are disclosed. The method of the present invention undertakes a hydrolytic condensation/polymerization reaction of penta(alkanol)alkoxy disiloxane, a reactive silicon-containing polymer and a reactive hydrophilic monomer to form a silicon-containing preploymer featuring a 3D network structure and having superior mechanical strength. The method further undertakes a copolymerization reaction of the silicon-containing preploymer, a hydrophilic monomer and a silicon-containing hydrophobic monomer to fabricate a silicone hydrogel-containing mixture having high oxygen permeability and high hydrophilicity. The silicone hydrogel-containing mixture can be used to fabricate contact lenses that the users wear comfortably.

11 Claims, 2 Drawing Sheets

3D NETWORK-STRUCTURED SILICON-CONTAINING PREPOLYMER AND METHOD FOR FABRICATING THE SAME

CROSS REFERENCE TO RELATED APPLICATION

This application is a Continuation-in Part of co-pending application Ser. No. 14/202,144, filed on Mar. 10, 2014, currently pending, for which priority is claimed under 35 U.S.C. §120 and the entire contents of all of which are hereby incorporated by reference.

BACKGROUND OF THE INVENTION

1. Field of the Invention

The present invention relates to a silicon-containing preploymer, particularly to a 3D network-structured silicon-containing preploymer, with a terminal of hydrophilic chains, i.e. a silicon-containing preploymer with an internal section of silicon-containing chains and an external section of hydrophilic chains, which is applicable to fabricate silicone hydrogel contact lenses.

2. Description of the Related Art

In addition to stability, non-toxicity and deposition-proofness, PMMA (polymethyl methacrylate) has superior optical properties and is abundant in source and cheap in price. Therefore, PMMA is the first plastic material used to fabricate contact lenses. However, PMMA is disadvantaged by poor hydrophilicity and poor oxygen permeability, which impairs the application of PMMA to contact lenses.

PHEMA (poly(2-hydroxyethyl methacrylate)) proposed by Witchterle and Lim is the first hydrogel used as biomedical material. PHEMA is a 3D network-structured polymer, swelling but insoluble in water. PHEMA has been widely used in biomedicine, especially in contact lenses. However, PHEMA is disadvantaged in low balanced water content and poor oxygen permeability, which has long limited the application of PHEMA. Therefore, many researchers have developed copolymers of PHEMA and hydrophilic monomers to overcome the abovementioned disadvantages of PHEMA.

The related manufacturers had persistently studied and researched the ways to improve comfort of users wearing hydrogel contact lenses and finally developed a plasma-based surface modification technology. The manufacturers use the technology and hydrophilic materials to improve the hydrophilicity of the surfaces of contact lenses with the oxygen permeability of silicone hydrogel being preserved. However, the technology needs expensive equipment and complicated processes. Besides, the technology cannot achieve stable bonding of the hydrophilic material and the surface of the silicone hydrogel and thus cannot achieve uniform quality, stable yield and low fabrication cost.

Based on theories and many years' experience in the related field, the Inventor had been persistently devoted to studying and researching the abovementioned problems and finally developed a 3D network-structured silicon-containing preploymer to overcome the abovementioned problems. The principles and embodiments of the present invention will be described in detail below.

SUMMARY OF THE INVENTION

The primary objective of the present invention is to provide a 3D (3-Dimensional) network-structured silicon-containing preploymer and a method for fabricating the same, wherein the preploymer mainly contains a highly oxygen-permeable hydrophobic silicone with a terminal of hydrophilic chains, i.e. a silicon-containing preploymer with an internal section of silicon-containing chains and an external section of hydrophilic chains, whereby the hydrophilic biomedical material is integrated with the hydrophobic material to improve water retention and comfortability of contact lenses, and whereby the problem that hydrophilic materials and hydrophobic materials are hard to bond together and likely to have phase separation is overcome.

Another objective of the present invention is to provide a 3D network-structured silicon-containing preploymer and a method for fabricating the same, wherein a simple hydrolytic condensation/polymerization reaction is used to fabricate a silicon-containing preploymer having 3D network structure and superior mechanical properties.

A further objective of the present invention is to provide a 3D network-structured silicon-containing preploymer and a method for fabricating the same, wherein a radical chain copolymerization reaction of hydrophilic monomers and hydrophobic monomers is used to form a silicone hydrogel having superior oxygen permeability, hydrophilicity and mechanical properties and exempted from low elongation and high brittleness, whereby the silicone hydrogel can be used to fabricate contact lenses having high oxygen permeability and superior comfortability.

To achieve the abovementioned objectives, the present invention proposes a 3D network-structured silicon-containing preploymer expressed by Formula (I):

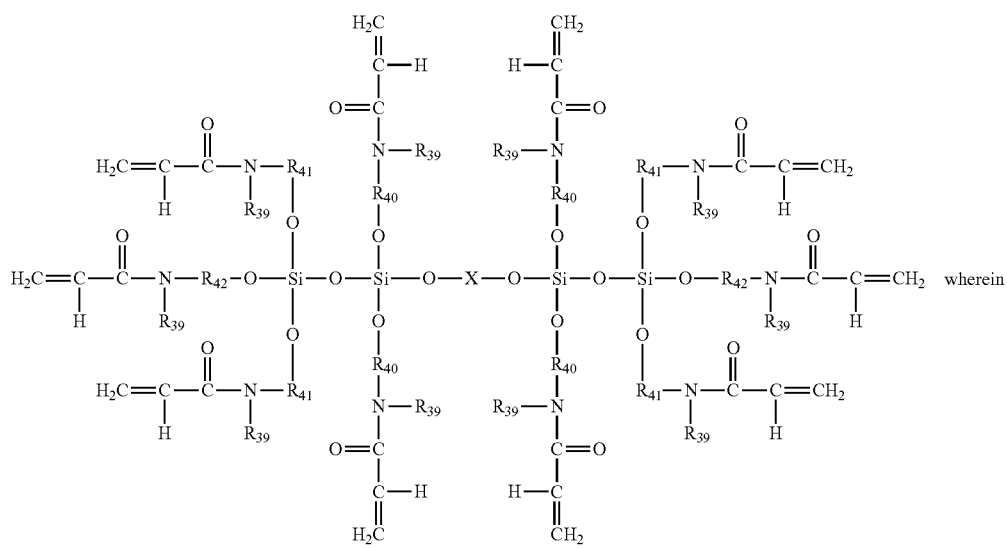

wherein

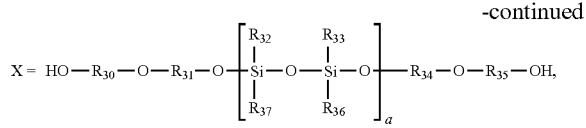

and wherein $R_{39}$ is a C1-C10 alkyl group; each of $R_{40}$, $R_{41}$ and $R_{42}$ is a C1-C8 alkylene group; each of $R_{30}$, $R_{32}$, $R_{33}$, $R_{35}$, $R_{36}$, and $R_{37}$ is a C1-C10 alkyl group; each of $R_{31}$ and $R_{34}$ is a C1-C8 alkylene group; a is an integer selected from 1 to 100.

The present invention also proposes a method for fabricating a 3D network-structured silicon-containing preploymer, which comprises steps mixing penta(alkanol)alkoxy disiloxane and a reactive silicon-containing polymer by a molar ratio of 1-50:1 to form a precursor of a siloxane; and mixing the siloxane precursor and a reactive hydrophilic monomer by a molar ratio of 1:1-40 to form a silicon-containing preploymer expressed by Formula (I).

In some embodiments, the silicon-containing preploymer is reacted with a hydrophilic monomer and a silicon-containing hydrophobic monomer to fabricate a silicone hydrogel-containing mixture. The silicone hydrogel-containing mixture is further fabricated into silicone hydrogel contact lenses having high oxygen permeability and superior comfortability.

Below, the embodiments are described in detail in cooperation with the attached drawings to make easily understood the objectives, technical contents, characteristics and accomplishments of the present invention.

DETAILED DESCRIPTION OF THE INVENTION

The summary hereinbefore and the detailed description thereinafter are used to demonstrate the spirit and principles of the present invention and interpret the claims of the present invention. The characteristics, applications and efficacies of the present invention will be described in further detail with embodiments and drawings below.

The HEMA-based soft contact lenses are fabricated mainly via synthesizing hydrophilic monomers, feathering high water content but disadvantaged by low oxygen permeability. The eyes will be irritated after wearing the contact lenses for hours. Thus, the time of wearing the contact lenses is limited. The present invention successfully overcomes the immiscibility of hydrophilic monomers and hydrophobic monomers and proposes a method of synthesizing silicon-containing monomers (hydrophobic monomers) and hydrophilic monomers to fabricate a silicon-containing preploymer featuring high oxygen permeability, high hydrophilicity and high transparency as a material of silicone hydrogel contact lenses, whereby users can wear the contact lenses comfortably for longer time.

Figure 1:
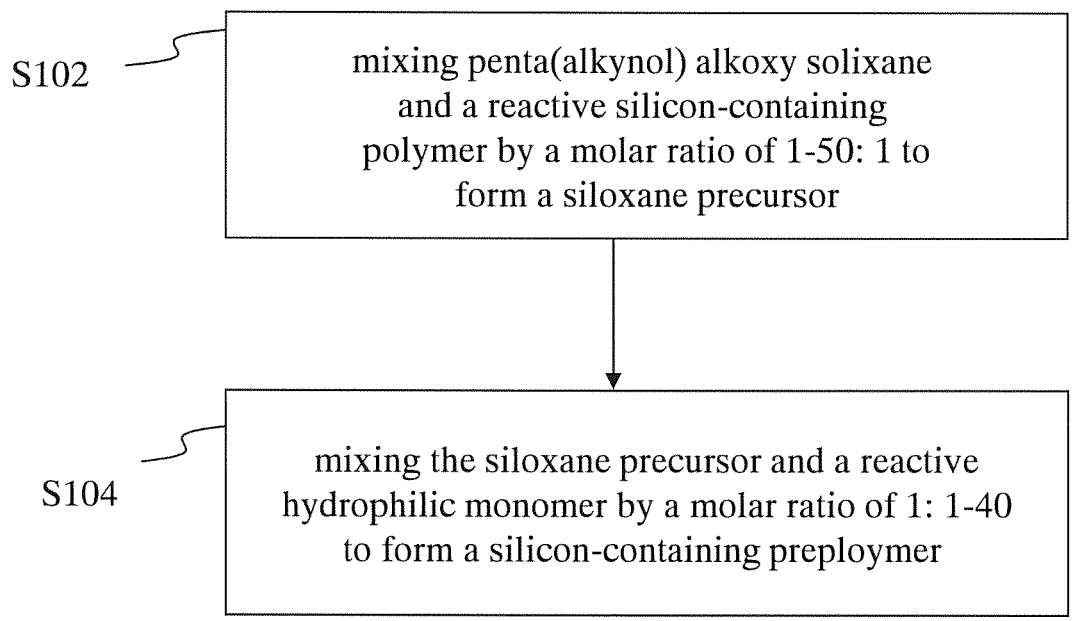
FIG. 1 is a flowchart of a method for fabricating a silicon-containing preploymer according to a first embodiment of the present invention.

Refer to FIG. 1 for a flowchart of a method for fabricating a silicon-containing preploymer according to a first embodiment of the present invention. As shown in FIG. 1, the method of the present invention comprises Step S102 and Step S104.

In Step S102, mix penta(alkanol)alkoxy disiloxane and a reactive silicon-containing polymer to form a precursor of a siloxane. In some embodiments, penta(alkanol)alkoxy disiloxane is expressed by Formula (II):

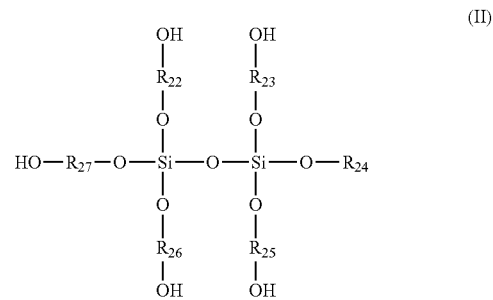

wherein each of $R_{22}$, $R_{23}$, $R_{25}$, $R_{26}$ and $R_{27}$ is a C1-C12 alkylene group, and $R_{24}$ is a C1-C12 alkyl group. The reactive silicon-containing polymer is expressed by Formula (III):

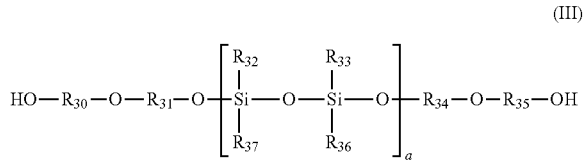

wherein each of $R_{30}$, $R_{32}$, $R_{33}$, $R_{35}$, $R_{36}$, and $R_{37}$ is a C1-C10 alkyl group; each of $R_{31}$ and $R_{34}$ is a C1-C8 alkylene group; a is an integer selected from 1 to 100. In Step S102, the molar ratio of penta(alkanol)alkoxy disiloxane and the reactive silicon-containing polymer is 1-50:1.

In some embodiments, the molar ratio of penta(alkanol) alkoxy disiloxane and the reactive silicon-containing is preferably 5-30:1, more preferably 7-20:1. The reaction in Step S102 is expressed by Equation (a):

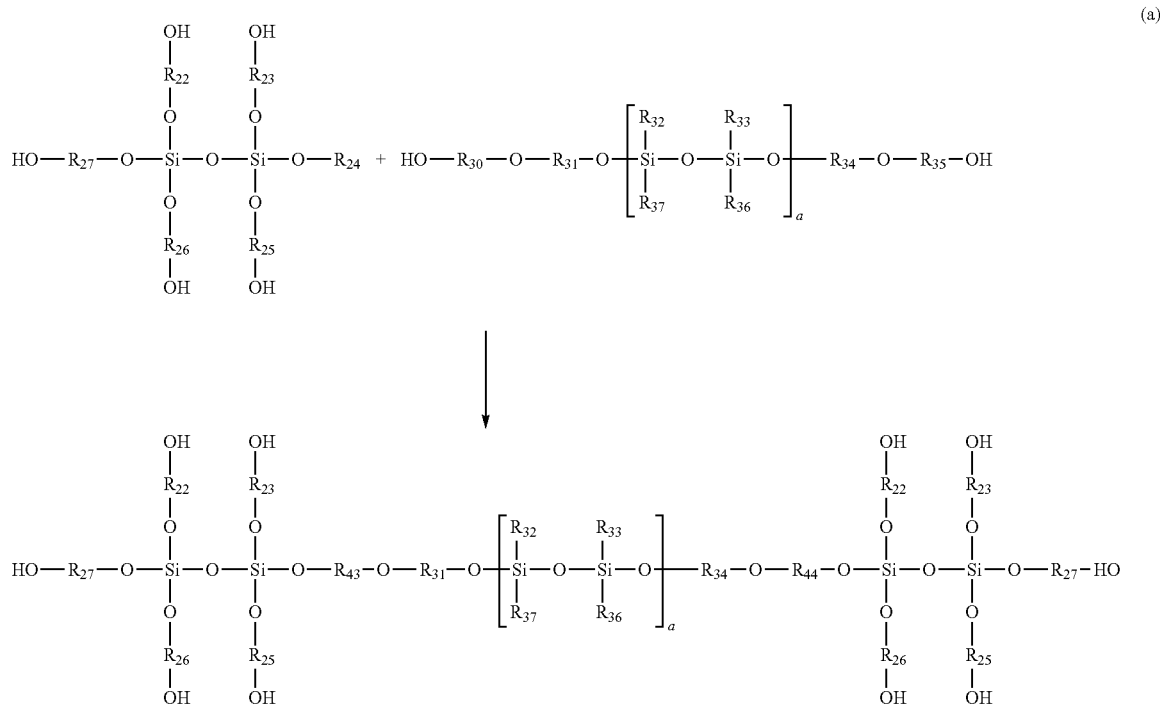

(a)

wherein each of $R_{22}$, $R_{23}$, $R_{25}$, $R_{26}$ and $R_{27}$ is a C1-C12 alkylene group, and $R_{24}$ is a C1-C12 alkyl group; each of $R_{30}$, $R_{32}$, $R_{33}$, $R_{35}$, $R_{36}$, and $R_{37}$ is a C1-C10 alkyl group; each of $R_{31}$, $R_{34}$, $R_{43}$, and $R_{44}$ is a C1-C8 alkylene group; a is an integer selected from 1 to 100.

In some embodiments, each of $R_{22}$, $R_{23}$, $R_{24}$, $R_{25}$, $R_{26}$ and $R_{27}$ in penta(alkanol)alkoxy disiloxane is preferably a C1-C10 alkylene group, more preferably a C1-C8 alkylene group. In some embodiments, penta(alkanol)alkoxy disiloxane is used as a reactant.

In some embodiments, each of $R_{30}$, $R_{32}$, $R_{33}$, $R_{35}$, $R_{36}$, and $R_{37}$ in the reactive silicon-containing polymer is preferably a C1-C10 alkyl group, more preferably a C1-C8 alkyl group. It is preferred that each of $R_{31}$, $R_{34}$, $R_{43}$, and $R_{44}$ in the reactive silicon-containing polymer is a C1-C8 alkylene group. In some embodiments, each of $R_{31}$ and $R_{34}$ in the reactive silicon-containing polymer is preferably a C1-C8 alkylene group, more preferably a C1-C6 alkylene group. In some embodiments, a reactive silicon-containing polymer PDMS-diol (poly(dialkylsiloxane)dialkanol) having a molecular weight of 2000-8000 is used as a reactant.

In Step S104, mix the siloxane precursor (the product of Equation (a)) and a reactive hydrophilic monomer to form a silicon-containing prepolymer. In Step S104, the molar ratio of the siloxane precursor and the reactive hydrophilic monomer is 1:1-40. In some embodiments, the molar ratio of the siloxane precursor and the reactive hydrophilic monomer is preferably 1:2-30, more preferably 1:3-20. The reaction in Step S104 is expressed by Equation (b):

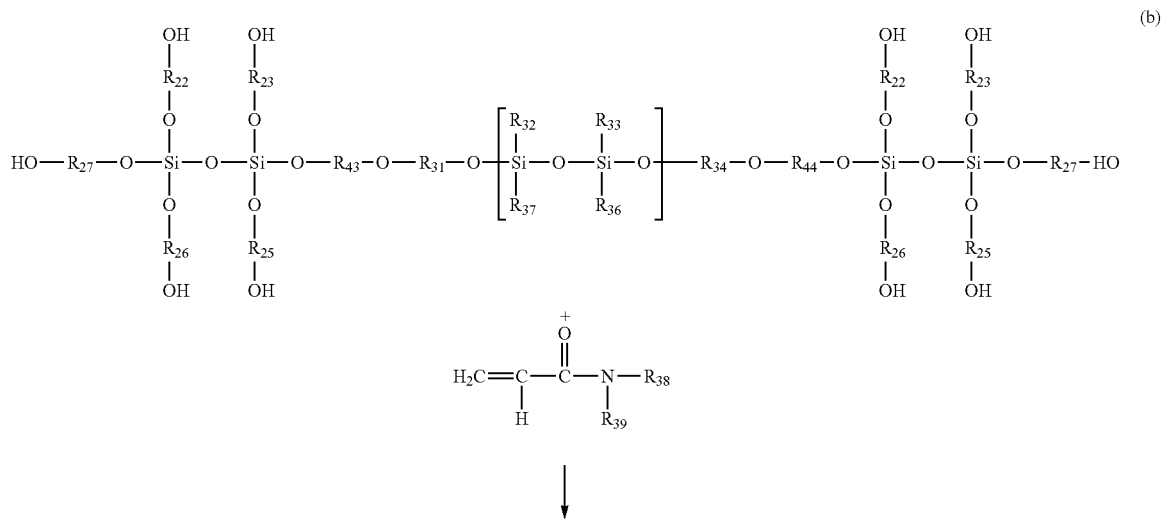

(b)

-continued

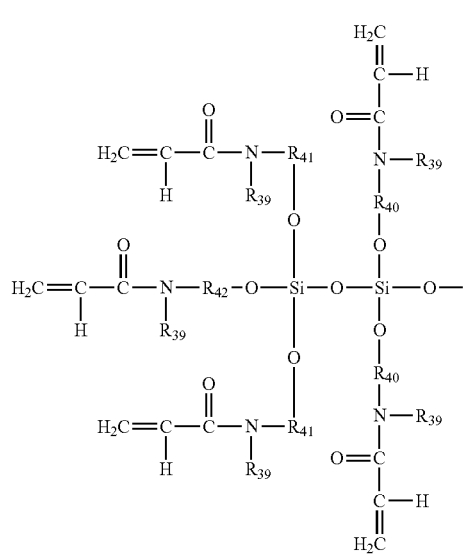
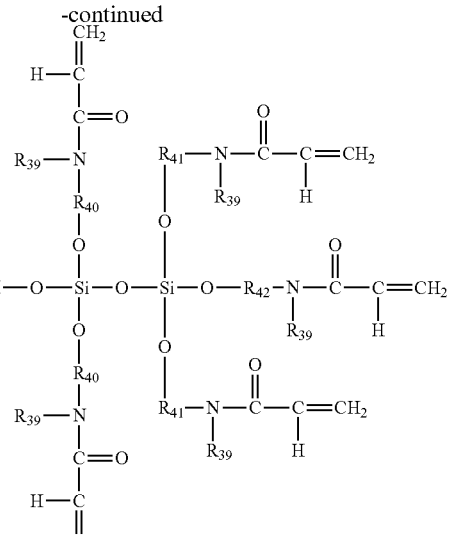

In some embodiments, the reactive hydrophilic monomer is expressed by Formula (IV):

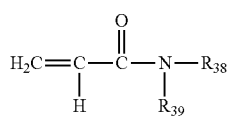

(IV)

wherein $R_{39}$ is a C1-C10 alkyl group; $R_{38}$ is a C1-C8 alkyl group or a carboxylic group. In some embodiments, $R_{39}$ in the reactive hydrophilic monomer is preferably a C1-C8 alkyl group, more preferably a C1-C6 alkyl group.

In some embodiments, $R_{38}$ in the reactive hydrophilic monomer is preferably a C1-C6 alkyl group or a carboxylic group, more preferably a C1-C3 alkyl group or a carboxylic group. In some embodiments, DMA (N,N-dimethylacrylamide) is used as the reactive hydrophilic monomer.

In the present invention, the abovementioned three reactants penta(alkanol)alkoxy disiloxane, the reactive silicon-containing polymer and the reactive hydrophilic monomer) are mixed sequentially to undertake a hydrolytic condensation/polymerization reaction under a weakly acidic or weakly alkaline environment according to Equations (a) and (b) and obtain a 3D network-structured silicon-containing prepolymer expressed by Formula (I):

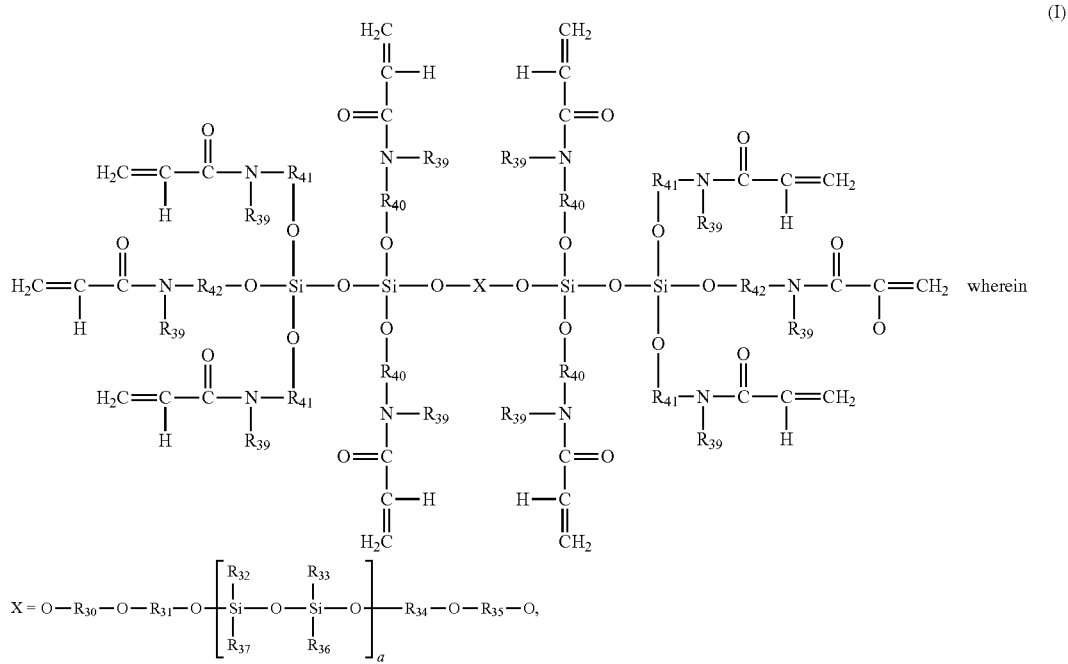

(I)

wherein and wherein $R_{39}$ is a C1-C10 alkyl group; each of $R_{40}$, $R_{41}$, and $R_{42}$ is a C1-C8 alkylene group; each of $R_{30}$, $R_{32}$, $R_{33}$, $R_{35}$, $R_{36}$, and $R_{37}$ is a C1-C10 alkyl group; each of $R_{31}$ and $R_{34}$ is a C1-C8 alkylene group; a is an integer selected from 1 to 100.

In some embodiments, the hydrolytic condensation/polymerization reaction is undertaken at a temperature of 10-70° C. and an environment having a pH value of 2-6 or 8-11 for 6-72 hours. It is preferred that the hydrolytic condensation/polymerization reaction is undertaken at a temperature of 20-40° C. and an environment having a pH value of 3-5 or 9-10 for 10-48 hours.

Thus, the 3D network-structured silicon-containing preploymer disclosed in the present invention is distinct from the chain type silicon-containing preploymer available in the market. The 3D network structure contributes superior mechanical strength to the silicon-containing preploymer of the present invention. Besides, the present invention uses different molar ratios of reactants to synthesize the silicon-containing prepolymers, whereby the silicon-containing prepolymers may have different ratios of unsaturated functional groups, wherefore the silicon-containing prepolymers of the present invention have better reactivity.

Figure 2:
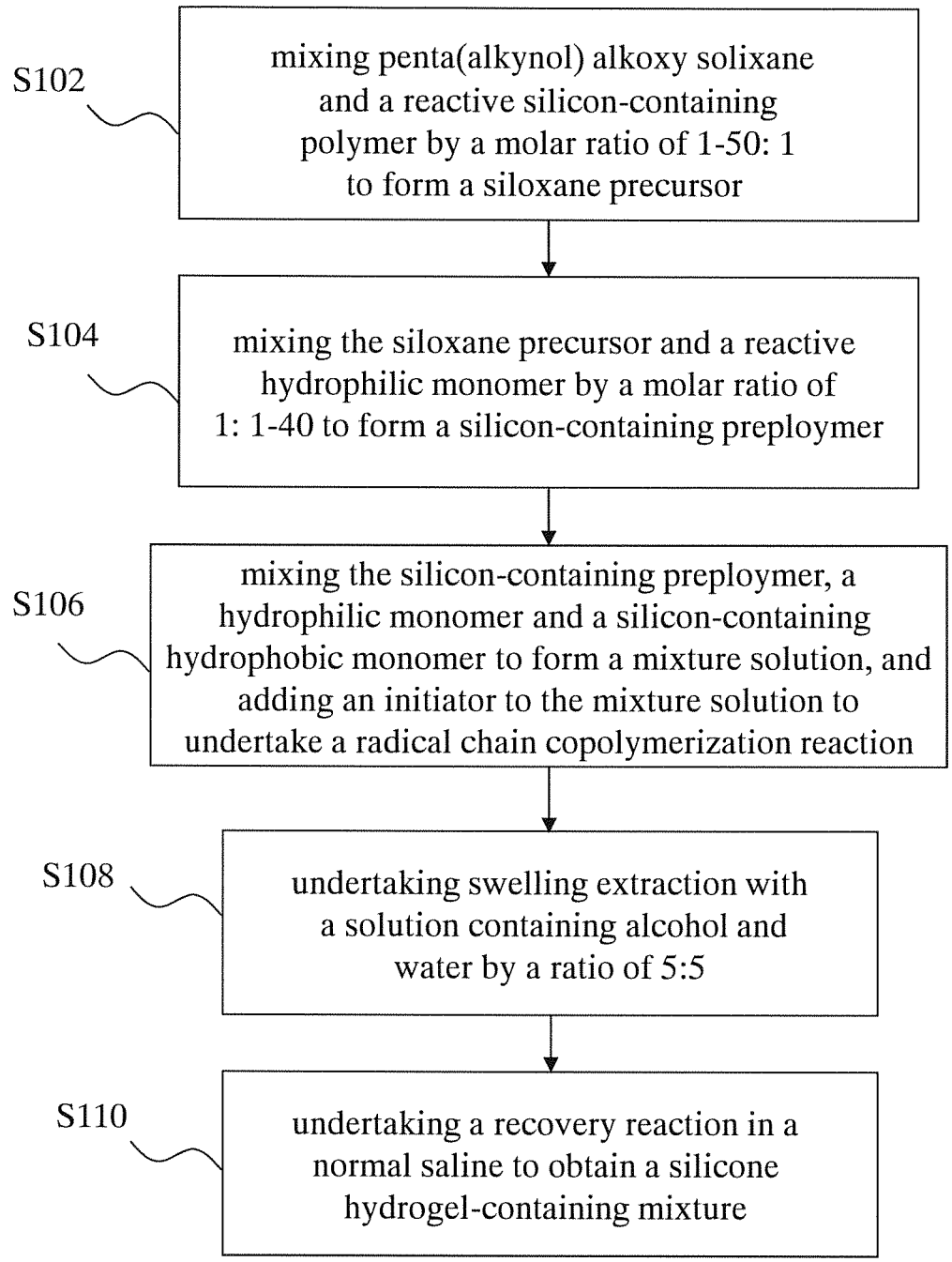
FIG. 2 is a flowchart of a method for fabricating a silicone hydrogel-containing mixture according to a second embodiment of the present invention.

In some embodiments, the silicon-containing preploymer of the present invention further reacts with a hydrophilic monomer and a silicon-containing hydrophobic monomer to form a silicone hydrogel-containing mixture. Refer to FIG. 2 for a flowchart of a method for fabricating a silicone hydrogel-containing mixture according to one embodiment of the present invention, wherein the method further comprises Step S106, Step S108 and Step S110 in addition Step S102 and Step S104.

Succeeding to Step S102 and Step S104, the process of the method of the second embodiment proceeds to Step S106. In Step S106, mix the silicon-containing preploymer, a hydrophilic monomer and a silicon-containing hydrophobic monomer to form a mixture solution, and then add an initiator to the mixture solution to undertake a radical chain copolymerization reaction. In Step S108, undertake swelling extraction with a solution containing alcohol and water by a ratio of 5:5. In Step S110, undertake a recovery reaction of the solution in a normal saline to obtain a silicone hydrogel-containing mixture.

In the present invention, the concentration of the silicon-containing preploymer in the silicone hydrogel-containing mixture is 1-65 wt %, preferably 10-60 wt %, more preferably 15-50 wt %; the concentration of the hydrophilic monomer is 1-65 wt %, preferably 10-55 wt %, more preferably 15-45 wt %; the concentration of the silicon-containing hydrophobic monomer is 1-70 wt %, preferably 10-55 wt %, more preferably 15-40 wt %. The silicon-containing hydrophobic monomer is selected from a group consisting of TRIS (tris(trimethylsiloxy)silylpropyl methacrylate), bis(trimethylsiloxy)methylsilylpropyl methacrylate, pentamethyldisiloxanyl methylmethacrylate, TSMC (tris(trimethylsiloxy)silylpropyl methacryloxyethylcarbamate), SIGMA (tris(trimethylsiloxy)silylpropyl glycerol methacrylate), tris(polydimethylsiloxy)silylpropyl methacrylate, and the combinations thereof. The hydrophilic monomer is selected from a group consisting of HEMA (hydroxyethyl methacrylate), glycerol methacrylate, MAA (methacrylic acid), NVP (N-pyrrolidone), N-isopropylacrylamide, 2-hydroxyethyl acrylate, N,N-diethylacrylamide, DMA (N,N-dimethylacrylamide), vinyl acetate, N-acryloylmorpholine, 2-dimethylaminoethyl acrylate, and the combinations thereof. In some embodiments, the silicon-containing hydrophobic monomer is TRIS, and the hydrophilic monomer is HEMA, MMA, or GMA.

The initiator used in Step S106 is a photo initiator or a thermal initiator, which may be any existing initiator. In some embodiments, the initiator is a photo initiator 2-Hydroxy-2-methyl-1-pentyl-1-propanone. In some embodiments, the initiator is a thermal initiator AIBN (Azobisisobutyronitrile). While a photo initiator is used as the initiator in Step S106, the radical chain polymerization reaction is undertaken under an illumination of 2-12 mW/cm$^2$, preferably 4-10 mW/cm$^2$.

From the above description, it is learned that the method for fabricating a silicone hydrogel-containing mixture of the present invention comprises steps: mixing a silicon-containing prepolymer, a silicon-containing hydrophobic monomer (TRIS), and a hydrophilic monomer (HEMA, MMA, or GMA) and agitating them uniformly to form a mixture solution; adding isopropanol and 2-Hydroxy-2-methyl-1-pentyl-1-propanone into the mixture solution to respectively function as the dispersing agent and the photo initiator and undertaking a radical chain copolymerization reaction under an illumination of 6 mW/cm$^2$ for 1 hour to form a silicone hydrogel; using a solution containing alcohol and water by a ratio of 5:5 to undertake swelling extraction of the silicone hydrogel for 3-4 hours; undertaking a recovery reaction of the product of the swelling extraction for 2-3 hours to obtain a silicone hydrogel-containing mixture. Then, pour the silicone hydrogel-containing mixture into a mold having a concaved surface, and use a spin thermalization process to shape the front surface of a contact lens. Alternatively, pour the silicone hydrogel-containing mixture into a female mold and a male mold, which respectively shape the front surface and the rear surface of a contact lens. Next, use light or heat to cure the silicone hydrogel-containing mixture. Then, a contact lens made of the silicone hydrogel-containing mixture is obtained.

The above description has fully demonstrated the 3D network-structured silicon-containing preploymer and the method for fabricating the same. Embodiments and experiments will be used to verify efficacies of the present invention below.

In different embodiments (E1-E8), the present invention uses different ratios of penta(alkanol)alkoxy disiloxane, a reactive silicon-containing polymer, a reactive hydrophilic monomer and acetic acid to fabricate silicon-containing preploymers, as shown in Table.1.

TABLE 1

| penta (alkanol) alkoxy disiloxane penta (alkanol) alkoxy disiloxane (mol) | Reactive Si-containing Polymer PDMS-diol (mol) | Reactive Hydrophilic Monomer DMA (mol) | Acetic Acid Solution in the first hydrolytic condensation/ polymerization reaction (μl) | Acetic acid Solution in the second hydrolytic condensation/ polymerization reaction (μl) |
|---|---|---|---|---|
| E 1    0.2 | 0.2 | 1 | 200 | 200 |
| E 2    0.3 | 0.2 | 1 | 200 | 200 |
| E 3    0.4 | 0.2 | 1 | 300 | 350 |
| E 4    0.5 | 0.2 | 1 | 300 | 350 |
| E 5    0.2 | 0.2 | 2 | 200 | 200 |
| E 6    0.3 | 0.2 | 2 | 200 | 200 |
| E 7    0.4 | 0.2 | 2 | 300 | 400 |
| E 8    0.5 | 0.2 | 2 | 300 | 400 |

In different applications (A1-A12), the present invention mixes the silicon-containing preploymers fabricated according to Table.1 with different ratios of a silicon-containing hydrophobic monomer, hydrophilic monomers and a photo initiator to fabricate silicone hydrogel contact lenses. The concentrations by weight percentage thereof are shown in Table.2.

TABLE 2

| | Silicon-Containing Preploymer Mixture Solution B (wt %) | Silicon-containing Hydrophobic Monomer PDMS (wt %) | Hydrophilic Monomers HEMA/DMA/GMA (wt %) | Photo Initiator D1173 (wt %) |
|---|---|---|---|---|
| A 1 | E 1 | 30 | 25/10/15 | 0.5-1.5 |
| A 2 | E 1 | 30 | 10/25/15 | 0.5-1.5 |
| A 3 | E 1 | 30 | 15/25/10 | 0.5-1.5 |
| A 4 | E 3 | 30 | 25/10/15 | 0.5-1.5 |
| A 5 | E 3 | 30 | 10/25/15 | 0.5-1.5 |
| A 6 | E 3 | 30 | 15/25/10 | 0.5-1.5 |
| A 7 | E 5 | 30 | 25/10/15 | 0.5-1.5 |
| A 8 | E 5 | 30 | 10/25/15 | 0.5-1.5 |
| A 9 | E 5 | 30 | 15/25/10 | 0.5-1.5 |
| A 10 | E 7 | 30 | 25/10/15 | 0.5-1.5 |
| A 11 | E 7 | 30 | 10/25/15 | 0.5-1.5 |
| A 12 | E 7 | 30 | 15/25/10 | 0.5-1.5 |

Then, the samples fabricated in Applications 1-12 are used to test the contact angles, water contents, oxygen permeabilities, and mechanical strengths. The contact angles are tested with a sessile drop method; the water contents are tested according to ISO standard 10399; the oxygen permeabilities are tested according to ISO9931-1; the mechanical strengths (elongations and elastic moduli) are tested according to ASTM D1780. From Table.3, it is learned: the contact angles of the silicone hydrogels of the present invention range from 40 to 60 degrees. Therefore, the silicone hydrogels have fine surface wettabilities and are suitable to fabricate contact lenses. From Table.3, it is also learned: the water contents of the silicone hydrogels range from 40-70%; the oxygen permeabilities (Dk) of the silicone hydrogels range from 40-100 barrers, which are obviously greater than the oxygen permeability of the HEMA contact lenses—the most popular contact lenses in the current market. From Table.3, it is also learned: the elongations of the silicone hydrogels of the present invention range from 80-200%, which indicates that the silicone hydrogels of the present invention completely escapes from the brittleness that the conventional products are likely to have. Therefore, the silicone hydrogels of the present invention are less likely to be fractured by tensile force. From Table.3, it is also learned: the elastic moduli the silicone hydrogels of the present invention are all below 1 MPa, which means that the users will wear the contact lenses made of the silicone hydrogels of the present invention comfortably.

TABLE 3

| | Contact Angle (°) | Water Content (wt %) | Oxygen Permeability (Dk) | Elongation (%) | Elastic Modulus (MPa) |
|---|---|---|---|---|---|
| A 1 | 58 ± 4 | 43.2 ± 1.3 | 47.3 ± 6.4 | 111 ± 18 | 0.699 ± 0.041 |
| A 2 | 57 ± 4 | 39.5 ± 1.5 | 51.8 ± 5.2 | 126 ± 11 | 0.861 ± 0.069 |
| A 3 | 54 ± 3 | 54.1 ± 1.6 | 55.3 ± 3.2 | 96 ± 11 | 0.813 ± 0.055 |
| A 4 | 58 ± 4 | 42.9 ± 1.1 | 57.9 ± 6.6 | 152 ± 15 | 0.706 ± 0.048 |
| A 5 | 56 ± 4 | 40.6 ± 1.2 | 60.1 ± 5.3 | 155 ± 19 | 0.711 ± 0.044 |
| A 6 | 55 ± 4 | 53.8 ± 1.8 | 48.3 ± 5.1 | 143 ± 13 | 0.813 ± 0.067 |
| A 7 | 58 ± 4 | 53.9 ± 1.5 | 55.4 ± 5.1 | 166 ± 21 | 0.612 ± 0.035 |
| A 8 | 52 ± 3 | 48.8 ± 1.5 | 47.1 ± 4.6 | 150 ± 20 | 0.737 ± 0.038 |
| A 9 | 44 ± 2 | 51.0 ± 1.9 | 51.3 ± 4.2 | 145 ± 17 | 0.611 ± 0.052 |
| A 10 | 55 ± 3 | 56.1 ± 1.6 | 61.7 ± 4.9 | 125 ± 25 | 0.413 ± 0.028 |
| A 11 | 48 ± 2 | 61.5 ± 1.9 | 60.2 ± 4.3 | 156 ± 22 | 0.559 ± 0.031 |
| A 12 | 41 ± 2 | 64.3 ± 2.1 | 65.2 ± 4.1 | 132 ± 19 | 0.521 ± 0.052 |

In conclusion, the present invention uses a simple hydrolytic condensation/polymerization reaction to fabricate a 3D network-structured silicon-containing preploymer featuring superior mechanical strength. The present invention mixes the silicon-containing preploymer with a hydrophilic monomer and a silicon-containing hydrophobic monomer and undertakes a copolymerization reaction thereof to fabricate silicone hydrogel contact lenses having high oxygen permeability, high hydrophilicity, and high comfortability. The present invention integrates hydrophilic chains with hydrophobic chains to form a silicon-containing preploymer having hydrophilic chains on the surface thereof and hydrophobic chains in the interior thereof and thus solve the conventional problem of water-oil immobility. Besides, the silicone hydrogel of the present invention has high transparency. Therefore, the present invention has very high potential in the market.

The embodiments described above are to demonstrate the technical thought and characteristics of the present invention to enable the persons skilled in the art to understand, make, and use the present invention. However, these embodiments are not intended to limit the scope of the present invention. Any equivalent modification or variation according to the spirit of the present invention is to be also included within the scope of the present invention.

What is claimed is:

1. A 3D network-structured silicon-containing prepolymer expressed by Formula (I):

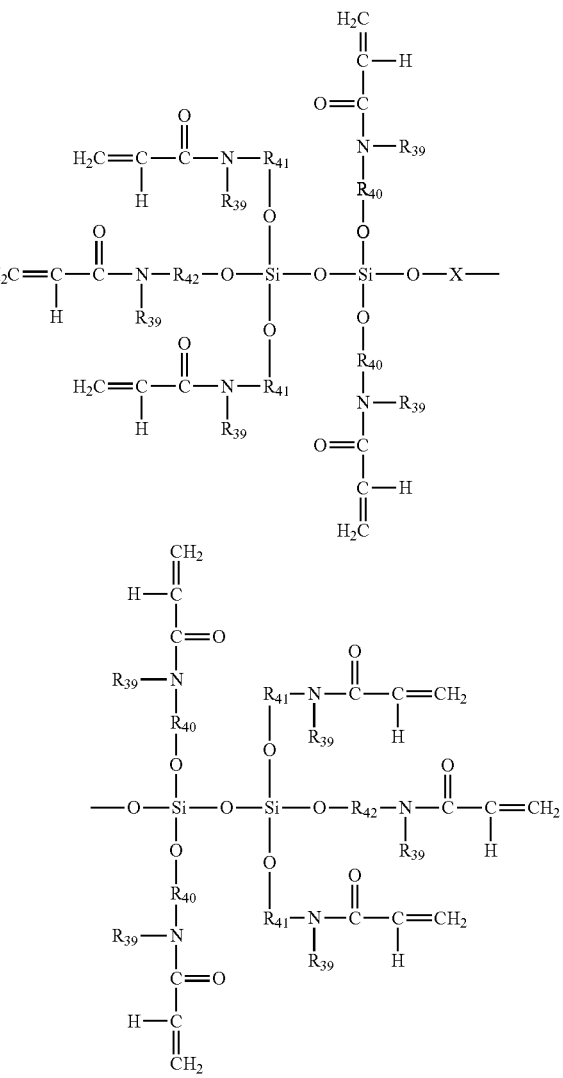

-continued

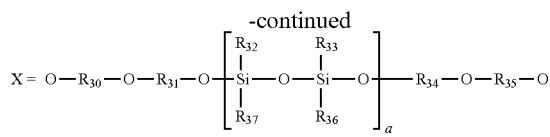

wherein $R_{39}$ is a C1-C10 alkyl group; each of $R_{40}$, $R_{41}$ and $R_{42}$ is a C1-C8 alkylene group; each of $R_{32}$, $R_{33}$, $R_{36}$, and $R_{37}$ is a C1-C10 alkyl group; each of $R_{30}$, $R_{31}$, $R_{34}$ and $R_{35}$ is a C1-C8 alkylene group; and a is an integer selected from 1 to 100.

2. A method for fabricating an article comprising the steps of:
mixing said silicon-containing prepolymer according to claim 1, a hydrophilic monomer and a silicon-containing hydrophobic monomer to form a mixture solution, and adding an initiator to said mixture solution to undertake a radical chain copolymerization reaction;
undertaking swelling extraction with a solution containing alcohol and water by a ratio of 5:5; and
undertaking a recovery reaction in a normal saline to obtain a silicone hydrogel-containing mixture.

3. The method for fabricating an article according to claim 2, wherein said initiator is a photo initiator or a thermal initiator.

4. The method for fabricating an article according to claim 3, wherein said photo initiator is 2-Hydroxy-2-methyl-1-pentyl-1-propanone.

5. The method for fabricating an article according to claim 4, which is undertaken under an illumination of 2-12 mW/cm².

6. The method for fabricating an article according to claim 3, wherein said thermal initiator is AIBN (azobisisobutyronitrile).

7. The method for fabricating an article according to claim 2, wherein said swelling extraction is undertaken with a solution containing alcohol and water by a ratio of 5:5 for 3-4 hours.

8. The method for fabricating an article according to claim 2, wherein said recovery reaction is undertaken in a normal saline for 2-3 hours.

9. The method for fabricating an article according to claim 2, wherein said silicon-containing hydrophobic monomer is selected from a group consisting of TRIS (tris(trimethylsiloxy)silylpropyl methacrylate), bis(trimethylsiloxy)methylsilylpropyl methacrylate, pentamethyldisiloxanyl methylmethacrylate, TSMC (tris(trimethylsiloxy)silylpropyl methacryloxyethylcarbamate), SIGMA (tris(trimethylsiloxy)silylpropyl glycerol methacrylate), tris(polydimethylsiloxy)silylpropyl methacrylate, and combinations thereof.

10. The method for fabricating an article according to claim 2, wherein said hydrophilic monomer is selected from a group consisting of HEMA (hydroxyethyl methacrylate), glycerol methacrylate, MAA (methacrylic acid), NVP (N-vinyl pyrrolidone), N-isopropylacrylamide, 2-hydroxyethyl acrylate, N,N-diethylacrylamide, DMA (N,N-dimethylacrylamide), vinyl acetate, N-acryloylmorpholine, 2-dimethylaminoethyl acrylate, and the combinations thereof.

11. A silicone hydrogel contact lens prepared by the method of claim 2.

* * * * *